US007268161B2

(12) United States Patent
Hinz

(10) Patent No.: US 7,268,161 B2
(45) Date of Patent: *Sep. 11, 2007

(54) COMPREHENSIVE PHARMACOLOGIC THERAPY FOR TREATMENT OF OBESITY INCLUDING CYSTEINE

(76) Inventor: Martin C. Hinz, 1150 - 88th Ave. West, Duluth, MN (US) 55808

( * ) Notice: Subject to any disclaimer, the term of this patent is extended or adjusted under 35 U.S.C. 154(b) by 72 days.

This patent is subject to a terminal disclaimer.

(21) Appl. No.: 10/886,156

(22) Filed: Jul. 6, 2004

(65) Prior Publication Data

US 2005/0065190 A1 Mar. 24, 2005

Related U.S. Application Data

(60) Division of application No. 09/947,941, filed on Sep. 6, 2001, now Pat. No. 6,759,437, which is a continuation-in-part of application No. 09/412,701, filed on Oct. 4, 1999, now Pat. No. 6,403,657.

(51) Int. Cl.
*A61K 31/34* (2006.01)
*A61K 37/44* (2006.01)
*A61K 31/13* (2006.01)

(52) U.S. Cl. ............ 514/469; 514/567; 514/663; 514/741; 514/905; 514/909

(58) Field of Classification Search ............ 514/910, 514/905, 469, 663, 567, 741, 909
See application file for complete search history.

(56) References Cited

U.S. PATENT DOCUMENTS

| | | | |
|---|---|---|---|
| 3,097,947 A | 7/1963 | Kemmerer | |
| 4,237,118 A | 12/1980 | Howard | 424/140 |
| 4,377,595 A | 3/1983 | Wurtman | |
| 4,397,866 A | 8/1983 | Wurtman | |
| 5,019,594 A | 5/1991 | Wurtman et al. | 514/561 |
| 5,084,007 A | 1/1992 | Malin et al. | |
| 5,189,064 A | 2/1993 | Blum et al. | |
| 5,480,657 A | 1/1996 | Allen | 424/617 |
| 5,527,788 A | 6/1996 | Svec et al. | |
| 5,650,438 A | 7/1997 | Meier et al. | |
| 5,795,895 A | 8/1998 | Anchors | 514/253 |
| 5,939,076 A | 8/1999 | Allocca | |
| 5,977,076 A | 11/1999 | Anderson et al. | |
| 5,977,099 A | 11/1999 | Nickolson | 514/214 |
| 6,048,728 A | 4/2000 | Inlow et al. | |
| 6,207,699 B1 | 3/2001 | Rothman | 514/419 |
| 6,261,589 B1 | 7/2001 | Pearson et al. | |
| 6,323,236 B2 | 11/2001 | McElroy | |
| 6,335,323 B2 | 1/2002 | Worsley | |
| 6,384,088 B1 | 5/2002 | Hinz | 514/909 |
| 6,403,657 B1 | 6/2002 | Hinz | 514/910 |
| 6,548,551 B2 | 4/2003 | Hinz | 514/663 |
| 6,660,777 B2 | 12/2003 | Hinz | |
| 6,759,437 B2 | 7/2004 | Hinz | 514/741 |
| 2001/0002269 A1 | 5/2001 | Zhao | |
| 2001/0008641 A1 | 7/2001 | Krotzer | |
| 2001/0008884 A1 | 7/2001 | Worsley | |
| 2001/0020007 A1 | 9/2001 | Wiss | |
| 2002/0040054 A1 | 4/2002 | Hinz | |
| 2002/0147206 A1 | 10/2002 | Howard, Jr. | |
| 2002/0187958 A1 | 12/2002 | Horrobin et al. | |
| 2003/0181509 A1 | 9/2003 | Hinz | |
| 2004/0071681 A1 | 4/2004 | Muller | |
| 2004/0077556 A1 | 4/2004 | Chinery | |
| 2004/0081678 A1 | 4/2004 | Cincotta | |
| 2004/0101575 A1 | 5/2004 | Hinz | |
| 2004/0116351 A1 | 6/2004 | Halevie-Goldman | |
| 2004/0151771 A1 | 8/2004 | Gin et al. | |
| 2004/0229285 A1 | 11/2004 | Hinz | |
| 2004/0247669 A1 | 12/2004 | Gin et al. | |
| 2005/0065190 A1 | 3/2005 | Hinz | |
| 2005/0233008 A1 | 10/2005 | Hinz | |
| 2005/0233014 A1 | 10/2005 | Lee et al. | |
| 2005/0287226 A1 | 12/2005 | Sisco et al. | |

FOREIGN PATENT DOCUMENTS

| | | |
|---|---|---|
| EP | 0347066 | 12/1989 |
| GB | 2137493 | 10/1984 |
| JP | 410067663 A | 3/1998 |
| WO | 01/26642 | 4/2001 |

OTHER PUBLICATIONS

Heath, "Pulmonary Vascular Disease" Medical Clinics of North America vol. 61(6), pp. 1279-1307 (1997).*
Hirsch, "The Treatment of Obesity with Drugs" The American Journal of Clinical Nutrition, pp. 2-4, (Jan. 1998).*
San Juan, Puerot Rico, Dec. 15, 2000 "PRNewswire".
*Brain Res* Jun. 12, 1999;831 (1-2):229-36, Transport mechanisms for the antidepressant citalopram in brain microvessal endothelium; written by B. Rochat, P. Baumann, KL Andus.

(Continued)

*Primary Examiner*—Vickie Kim
(74) *Attorney, Agent, or Firm*—Patterson, Thuente, Skaar & Christensen, P.A.

(57) ABSTRACT

The comprehensive pharmacologic therapy for treatment of obesity including Cysteine is a procedure which involves the administration of a desired therapeutic range of Diethylpropion and/or Phentermine in combination with a SSRI medication and nutritional supplementation for brief and long durations which may be 12 months or more. The preferred procedure involves the administration of drugs in combination which are identified as: Citalopram (Celexa) and Phentermine; Citalopram (Celexa) and Diethylpropion; Citalopram (Celexa), Phentermine, and Diethylpropion. In addition nutritional supplementation such as a multivitamin, 5-Hydroxytryptophan, Cysteine, vitamin B6, vitamin C, Tyrosine, Calcium, and Lysine may be used to enhance the performance of the weight loss treatment program.

18 Claims, 1 Drawing Sheet

OTHER PUBLICATIONS

*Psychomharmacol Bull* 1997;33(1):109-12, Plasma levels of citalopram enantiomers and metabolites in elderly patients; written by JP Foglia, BG Pollock, MA Kirshner, J Rosen, R Sweet, and B Mulsant.
Abstract from: *Clin Neuropharmacol* Mar.-Apr. 2000;23(2):90-7; Neuropharmacology of paradoxic weight gain with selective serotonin reuptake inhibitors; written by BH Harvey and CD Bower.
Abstract from: *Clin Psychiatry* 2000;61 Suppl 11(1-2):37-41, Weight gain and antidepressants; M Fava.
Abstract from: *J Clin Psychiatry* Nov. 2000;61(11):863-7, Fluoxetine versus sertraline and paroxetine in major depressive disorder: changes in weight with long-term treatment; written by M Fava, R Judge, SL Hoog, ME Nilsson, and SC Koke.
Abstract from: *Int clin psychopharmacol* Nov. 1999; 14(6):329-37; Efficacy and tolerability of mirtazapine versus citalopram: a double-blind, randomized study in patients with major depressive disorder. Nordic Antidepressant Study Group; written by E Leinonen, J Skarstein, K Behnke, H Agren, and JT Helsdingen.
Excerpt from: *Anchors* (US Patent 5,795,895) book, "Safer than Phen-fen", p. 82; written by Michael Anchors, M.D., Ph.D., Aug. 1998.
Budavari et al., *The Merck Index*, 1989, Merck & Co., Inc., 11$^{th}$ Edition, pp. 2321 and 4116.
Riley et al., *Facts and Comparisons®*, 1999, pp. 239, 264(d), and 264(td).
*The Medical Clinics of North America*, vol. 61/No. 6, Nov. 1977; Pulmonary Vascular Disease, written by Donald Heath and Paul Smith, pp. iii and 1279-1307.
*The American Journal of Clinical Nutrition*, Jan. 1998—vol. 67—No. 1; Treatment of Obesity with Drugs; written by Jules Hirsch.
*Archives of Internal Medicine*, Jan. 12, 1998, vol. 158, p. 102; Asymptomatic Mitral and Aortic Valve Disease Is Seen in Half of the Patients Taking 'Phen-Fen'; written by Griffen et al.
*The Medical Letter® On Drugs and Therapeutics*, vol. 36 (Issue 936), Nov. 25, 1994, pp. 107-108; Fluoxetine (Prozac) and Other Drugs for Treatment of Obesity.
*Archives of Internal Medicine*, May 11, 1998, vol. 158, pp. 1278-1279; The "Phen-Pro" Diet Drug Combination is Not Associated With Valvular Heart Disease; written by Griffen et al.
Deposition Transcripts of Dr. Martin C. Hinz (vol. I of Nov. 17, 2004; and vol. II of Feb. 24. 2005).
Deposition Transcripts of Gottfried Kellermann, which is also on behalf of Neuroscience (vol. I of Nov. 23, 2004; and vol. II of Nov. 24, 2004).
Deposition Transcript of Dr. William Wilson—Nov. 12, 2004.
Deposition Transcript of Dave Peterson—Feb. 28, 2005.
Abell et al., "Placebo Controlled Double-Blind Trial of Fluvoxamine Maleate in the Obese", *Journal of Psychosomatic Research*, 30(2): 143-164 (1986).
Bouchard et al. "Gitalopram and Viloxazine in the treatment of depression by means of slow drop infusion A double-linked comparative trial", *Journal of Affective Disorders*, 46:51-58 (1997).
Marek et al., "A comparison of trazodone and fluoxetine: implications for serotonergic mechanis of antidepressant action", *Psychopharmacology* 109:2-11 (1992).
Van Praag, "In Search of the Mode of Action of Antidepressants 5-HTP/Tyrosine Mixtures in Depressions", Neuropharmacology 22(38):443-440 (1983).
U.S. Appl. No. 09/523,114, filed Mar. 10, 2000, Hinz.
U.S. Appl. No. 11/282,965, filed Nov. 18, 2005, Hinz.
U.S. Appl. No. 11/353,644, filed Feb. 14, 2006, Hinz.
U.S. Appl. No. 11/353,643, filed Feb. 14, 2006, Hinz.
Agundez et al, "Modulation of CyP1A2 enzyme activity by indoleamines: inhibition by serotonin and tryptamine", *Pharmacogentics*, 8:251-258 (1998).
Andrews et al, "The Effects of 5-hydraoxytryptophan and 5-hydroxytryptamine on Dopamine Synthesis and Release in Rat Brain Striatal Synaptosomes", *Journal of Neurochemistry*, 30:465-470 (1978).
Avarello, "Serotonin Syndrome: a reported case", *Neuro Sci*, 23:S55-S56 (2002).
Bartholome et al., "L-dopa and 5-hydroxytryptophan Therapy in Phenylalanine-Hydroxylase Activity", *The Lancet* 2(Nov. 22): 1042-1043 (1975).
Bouyer et al., "Modification of Spontaneous ECoG and Behavior in Cat by Monoamine Precursors", *Psychopharmacology*, 65:49-54 (1979).
Coppen et al. "Levodopa and L-tryptophan Therapy in Parkinsonism", *The Lancet*, Mar. 25, (1972).
Dunner et al., "Affective Disorder: Studies with Amine Precursors", *Am J. Psychiatry*, 132(2):180-183 (1975).
Gelenberg et al. "Tyrosine for the treatment of depression", *Nutr. Health*, 3(3):163-73 (1984).
Hurley et al., Pyrrolo [1,4]benzodiazepine Antibiotics. Biosynthesis of the Antitumr Antibiotic 11-Demethyltomaymycin and its Biologically Inactive metabolity Oxotomaymycin to Streptomyces achromogene, *Biochemistry*, 15(17):3760-3769 (1976).
Kramarcy et al, "Effects of Drug-Inducted Changes in Brian Monoamines on Aggression and Motor Behavior in Mice", *European Journal of Pharmacology*, 99:141-151 (1984).
Li Kam Wa et al., "Renal metabolism and effects of the glutamyl derivates of L-dopa and 5-dydroxytryptophan in man", *Clinical Science*, 91:177-185 (1996).
Lindström, "Aromatic-L-Amino-Acid Decarboxylase Activity in Mouse Pancreatic Islets", Biochimica et Biophysica Acta, 884: 276-281 (1986).
Lindström et al., "Aromatic amino acids and pancreatic islet function: a comparison of L-tryptophan and L-5-hydroxytryptophan", *Molecular and Cellular Endocrinology*, 48: 121-126 (1986).
Malone et al., "Treatment (Rx) of 76 Pateitns with Primary Fibromyalgia (1° FM) with Combined Dopaminergic and Serotonergic Drugs", Arthritus & Rhuematism, 39:S92 (1996) (Abstract).
Mathiau et al, "Absence of Serotonergic Innervation form Raphe Nuclie in Rat Cerebral Blood Bessesl - II. Lack of Trypthophan Hydroxylase Activity *In Vitro*" Neuroscience, 52(3): 657-665 (1993).
Meyers, "Use of Neurotransmitter Precursors for Treatment of Depression", Alternative Medicine Review, 5(1): 64-71 (2000).
Niedens et al, "First fungal aromatic L-amino acid decarboxylase from a paclitaxel-producing Penicillium raistrickii", Mycologia, 91(4):61-26 (1999) (Abstract).
Rabey et al., "L-trypotphan Administration in L-Dopa-Induced Hallucinations in Elderly Parkinsonian Patients" Gerontology, 23: 438-444 (1977).
Sawaki et al., "Some correlations between Procaine-Induces Convulsions and Monamines in the Spinal Cord of Rats", *Japan, J. Pharmacol*, 51:369-376 (1989).
Schlosberg et al., "Effects of L-Dopa and L-5-Hydroxytryptophan on Locomotor Activity of the Rat after Selective or combined destruction of Central Catecholamine and Serotonin Neurons", *The Journal of Pharmacology and Experimental Therapeutics*, 211(2):296-304 (1979).
Shintaku et al., "Diagnosis and treatment of 6-pyruvoyl-tetrahydropterin synthase deficiency", *Brain & Development*, 22:S118-S121 (2000).
Sternberg et al, "Development of Scleroderma-like Illness during Therapy with L-5-hydroxytryptophan and Carbidopa", *The New England Journal of Medicine*, 303(14):782-787 (1980).
Tanaka et al., "Hyperphenylalaninemia Due to Impared Dihydrobiopterin Biosynthesis", *Eur. J. Pediatr*, 136:275-280 (1981).
Thurmond et al, "Effects of Dietary Tyrosine, Phenylamlanine, and Tryptophan on Aggression in Mice", *Pharmacoogy Biochemistry & Behavior*, 6:475-478 (1997).
Trulson et al., "Behavorial Effects of Serotonergic and Dopaminergic Drugs in Cats Following Chronic Amphetamine Administration", *European Journal of Pharmacology*, 99: 313-324 (1984).
Weitbrecht and et al., "Der Einfluss von l-Tryptophan auf die L-Dopa-Resportion", *Dtsch Med Wochenschr*, 101(1):20-22 (1976).
Dave Peterson Affidavit dated Apr. 11, 2005.

* cited by examiner

COMPREHENSIVE PHARMACOLOGIC THERAPY FOR TREATMENT OF OBESITY INCLUDING CYSTEINE

This application is a Divisional Application from application Ser. No. 09/947,941, filed Sep. 6, 2001 which will issue on Jul. 6, 2004, as U.S. Pat. No. 6,759,437, which application is a Continuation-In-Part Patent Application of application Ser. No. 09/412,701 filed Oct. 4, 1999, which issued as U.S. Pat. No. 6,403,657 on Jun. 11, 2002, the entire contents of which are hereby incorporated herein by reference in their entireties.

BACKGROUND OF THE INVENTION

Research has identified that long term use of medications for treatment of obesity in patients has resulted in many problems. The two most significant problems encountered by patients using medications to assist in weight loss, assuming the absence of irreversible side effects from the medications, are that:

The medications stop working during therapy where at least 40% to 50% of patients quit losing weight (plateau) on an average of 3.3 months into therapy; and 5% to 8% of patients who receive drug therapy for weight problems experience the complication where the medications fail to assist in appetite suppression where the patient therefore does not lose significant weight.

In the past long term treatment, defined as treatment longer than 3 months to many years, with medications, has raised safety issues including, medication intolerability by the patient, medication side effects and most important ineffectiveness of the drugs or the cessation of benefit of the drugs which in turn causes the patient to fall out of appetite suppression and terminate weight loss.

A weight loss procedure using SSRI medication is disclosed in U.S. Pat. No. 5,795,895. The potential for patients to obtain goal weight loss under the process of U.S. Pat. No. 5,795,895 is low, and the failure of the drugs to provide a desired level of performance is at the heart of the problem.

In the past obesity or weight management procedures, as noted in U.S. Pat. No. 5,795,895, implement a single dosing schedule of SSRI medication for a patient. A single dosing schedule of SSRI medication is not optimal for a desired level of weight loss performance. Individuals frequently fail to lose a desired amount of weight when alternative doses of medication are unavailable.

Second, patients receiving treatment for weight loss through the use of medication frequently experience complications such as a cessation of performance of the medication due to a "nutritional deficiency". Frequently it is difficult to predict which patients are likely to experience unacceptable performance of weight loss medication due to "nutritional deficiencies" associated with calorie deficit's.

It is also problematic to predict the outcome of medication treatment upon individuals receiving Norepinephrine medications such as Phentermine and/or Diethylpropion. These medications have unique chemical properties making the outcome of treatment of patients uncertain. In addition not all medications function to assist in weight loss. In the past SSRI (selective Serotonin Reuptake Inhibitor) medications which have been used in weight loss include Fluoxetine Hydrochloride (Prozac), Sertraline (Zoloft), Fluvoxamine Maleate (Luvox), and Trazodone Hydrochloride (Desyrel).

The treatment programs for obesity as known also teach away from the use of alternative dosing procedures to effectuate weight loss. Specifically U.S. Pat. No. 5,795,895 teaches that an SSRI medication never needs to be raised to improve the anorexiant effect of weight loss and that the SSRI medication level administered to a patient may be raised to assist in the treatment of coexisting conditions such as depression.

It is therefore desirable to have a weight loss treatment program for a patient which provides for an effective therapeutic range of available medication to enhance desired weight loss. It is also desirable to provide a weight loss program which minimizes the percent of individuals who do not initially respond to the medication treatment regime or who cease to continue to receive the beneficial effects of the weight loss program following the initiation of the medication treatment due to nutritional deficiencies. These and other problems are solved by the disclosed Comprehensive Pharmacologic Therapy For Treatment Of Obesity.

A problem has been known in the past where drugs which work on norepinephrine stop working after a period of time when used in treating patients for weight loss. As stated in Wurtman et. al in U.S. Pat. No. 4,885,312.

Indirect-acting sympathomimetic amines (such as Phentermine) function by releasing stored norepinephrine from sympathetic nerve endings. The major problem with their use is that after a few doses, they often stop functioning, i.e., tachyphylaxis sets in. Tachyphylaxis is known to be associated with partial depletion of the norepinephrine in the nerve endings, leading to the supposition that there are releasable and non-releasable pools of norepinephrine and that when the drugs cease functioning, it is because the releasable pools have been severely depleted. The chemical pathway involved is:

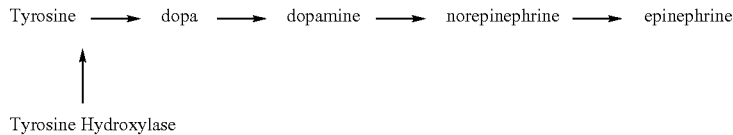

Dopa, doparnuie, norepinephrine, and epinephrine are known as "catecholamines". Chemically the enzyme "Tyrosine Hydroxylase" limits the rate of formation of catecholamines. Another problem as known is to identify a way to increase the amounts of Tyrosine Hydroxylase or it's activity in a patient receiving treatment for obesity. No procedure is known which uses a dietary precursor approach to increase amounts of Tyrosine Hydroxylase and it's activity in a patient receiving treatment for obesity. No procedure is known to increase catecholamine levels in a patient by providing the precursor needed for the formation of Tyrosine Hydroxylase.

Catecholamine formation is regulated by a feed back loop involving norepinephrine and Tyrosine Hydroxylase. In this loop norepinephrine binds to each of the four legs of the Tyrosine Hydroxylase enzyme and through the mechanism of phosphorylation the norepinephrine deactivates Tyrosine Hydroxylase into a new chemical known as "phosphorylated Tyrosine Hydroxylase". In the process the body begins to synthesis more Tyrosine Hydroxylase.

A complication in the treatment of patients for weight loss is that drugs which are given to increase the levels of intersynaptic norepinephrine lead to increased phosphorylation of Tyrosine Hydroxylase which, in turn, causes increased synthesis of Tyrosine Hydroxylase and depletion of critical precursors. The net effect of drugs which cause increased intersynaptic levels of norepinephrine for a patient is the depletion of precursors need in the synthesis of Tyrosine Hydroxylase leading to the "tachyphylaxis". The provision to a patient of the precursor Tyrosine with co-factors vitamin C, calcium, and vitamin B6 will not prevent or reverse the tachyphylaxis induced by drugs which cause increased levels of intersynaptic norepinephrine.

BRIEF DESCRIPTION OF THE INVENTION

The invention embodies the use of Phentermine and/or Diethylpropion with an SSRI medication, Citalopram. The SSRI medication is used in an "effective therapeutic range" to provide optimal results. The treatment enables individuals to have a much higher expectation of weight loss to achieve a desired weight than the previous known treatments. The method of weight loss enables individuals to lose weight optimally and safely. With treatment, as individuals lose weight other diseases or illnesses caused by or associated with weight problems get markedly better or resolve completely. These illnesses and/or diseases are identified as type II diabetes, hypertension, hypercholesterolemia, orthopedic problems, depression, anxiety, panic attacks, migraine headaches, PMS, chronic pain states, fibromyalgia, insomnia, sleep apnea, impulsivity, obsessive compulsive disorder, and myoclonus. Duration of treatment may be long term, or for life if needed, to reduce weight and maintain weight loss as desired by an individual.

The treatment of a patient for weight loss may include the use of Cysteine with precursors Tyrosine, 5-Hydroxytryptophan, vitamin C, vitamin B6, and calcium. Use of the precursors and co-factors of Cysteine generally insures that adequate direct precursors are available to increase catecholamine levels for a patient prolonging the effectiveness of medication therapy.

An advantage of the present invention is the provision of a comprehensive pharmacologic therapy for treatment of obesity of relatively simple and inexpensive design which fulfills the intended purpose of appetite suppression to enable weight loss without fear of injury to persons.

Another principal advantage of the present invention is the provision of a comprehensive pharmacologic therapy for treatment of obesity which is easy for patients to initiate and continue to effectuate weight loss.

Still another principal advantage of the present invention is the provision of a comprehensive pharmacologic therapy for treatment of obesity which is effective for all patients attempting to lose weight.

Still another principal advantage of the present invention is the provision of a comprehensive pharmacologic therapy for treatment of obesity which continues to function to enable patient weight loss following the initiation of therapy by an individual.

Still another principal advantage of the present invention is the provision of a comprehensive pharmacologic therapy for treatment of obesity which promotes appetite suppression while simultaneously maintaining nutritional balance for an individual.

Still another principal advantage of the present invention is the provision of a comprehensive pharmacologic therapy for treatment of obesity which minimizes risk of undesirable side effects for a patient.

Still another principal advantage of the present invention is the provision of a comprehensive pharmacologic therapy for treatment of obesity which may be used long term defined as a period of time exceeding three months.

Still another principal advantage of the present invention is the provision of a comprehensive pharmacologic therapy for treatment of obesity which minimizes risk of medication intolerability for a patient.

Still another principal advantage of the present invention is the provision of a comprehensive pharmacologic therapy for treatment of obesity which minimizes medication side effects and/or complications for a patient.

Still another principal advantage of the present invention is the provision of a comprehensive pharmacologic therapy for treatment of obesity which assists in empowering a patient to achieve a desired goal weight through monitored, healthy, and controlled weight loss.

Still another principal advantage of the present invention is the provision of a comprehensive pharmacologic therapy for treatment of obesity which is flexible to a patient's needs through the provision of an effective therapeutic range of weight loss medication.

Still another principal advantage of the present invention is the provision of a comprehensive pharmacologic therapy for treatment of obesity which minimizes risk of nutritional deficiency for a patient.

Still another principal advantage of the present invention is the provision of a comprehensive pharmacologic therapy for treatment of obesity which simultaneously treats other diseases or obesity related illnesses such as type II diabetes, hypertension, hypercholesterolemia, orthopedic problems, depression, anxiety, panic attacks, migraine headaches, PMS, chronic pain states, fibromyalgia, insomnia, sleep apnea, impulsivity, obsessive compulsive disorder, and/or myoclonus.

Still another advantage of the present invention is the provision of a comprehensive pharmacologic therapy for treatment of obesity which includes the regulated prescription of an SSRI medication namely, Citalopram in an effective therapeutic range for a patient to effectuate weight loss.

Still another advantage of the present invention is the provision of a comprehensive pharmacologic therapy for treatment of obesity which includes the regulated prescription of Phentermine in an effective therapeutic range for a patient to effectuate weight loss.

Still another advantage of the present invention is the provision of a comprehensive pharmacologic therapy for treatment of obesity which includes the regulated prescription of Diethylpropion in an effective therapeutic range for a patient to effectuate weight loss.

Still another advantage of the present invention is the provision of a comprehensive pharmacologic therapy for treatment of obesity which includes the consumption of 5-Hydroxytryptophan by a patient in an effective therapeutic range to assist in avoiding nutritional deficiencies and effectuating weight loss.

Still another advantage of the present invention is the provision of a comprehensive pharmacologic therapy for treatment of obesity which includes the consumption of Lysine by a patient in an effective therapeutic range to assist in avoiding nutritional deficiencies and effectuating weight loss.

Still another advantage of the present invention is the provision of a comprehensive pharmacologic therapy for treatment of weight loss which includes the consumption of vitamin B6 by a patient in an effective therapeutic range to assist in avoiding nutritional deficiency and effectuating weight loss.

Still another advantage of the present invention is the provision of a comprehensive pharmacologic therapy for treatment of obesity which includes the consumption of vitamin C by a patient in an effective therapeutic range to assist in avoiding nutritional deficiency and effectuating weight loss.

Still another advantage of the present invention is the provision of a comprehensive pharmacologic therapy for treatment of obesity which includes the consumption of Tyrosine by a patient in an effective therapeutic range to assist in avoiding nutritional deficiency and effectuating weight loss.

Still another advantage of the present invention is the provision of a comprehensive pharmacologic therapy for treatment of obesity which includes the consumption of a multi-vitamin by a patient to assist in avoiding nutritional deficiency and effectuating weight loss.

Still another advantage of the present invention is the provision of a comprehensive pharmacologic therapy for treatment of obesity which includes the consumption of calcium by a patient in an effective therapeutic range to assist in avoiding nutritional deficiency and effectuating weight loss.

Still another advantage of the present invention is the provision of a comprehensive pharmacologic therapy for treatment of obesity which includes the consumption of Lysine in an effective therapeutic range to assist in avoiding nutritional deficiency and effectuating weight loss.

Still another advantage of the present invention is the provision of a comprehensive pharmacologic therapy for treatment of obesity which involves consumption of citalopram by a patient for an initial six (6) day period of time at an initial dosage level where the dosage level may be subsequently modified after the initial six (6) day period of time to maximize likelihood of success of weight loss by a patient.

Still another advantage of the present invention is the provision of a comprehensive pharmacologic therapy for treatment of obesity which involves the monitoring of a patients weight loss progress through calculation of "low weight loss" as defined by a patient weight at a previous visit added to a patient current weight then divided by two (2) followed by multiplication by 10 and then less the current patient weight, less the patient weight at the previous visit, then multiplied by 3,500 and then divided by the number of days between the previous visit and the date of the current weight for the provision of a first sum; calculating a second sum by multiplying a patient goal weight times ten then divided by 0.8928; and comparing the first sum to the second sum where low weight loss occurs when said first sum is larger than said second sum.

Still another advantage of the present invention is the provision of Cysteine to a patient receiving treatment for weight loss to reverse the undesirable effects of tachyphylaxis due to the use of a drug which increases intersynaptic norepinephrine levels.

Still another advantage of the present invention is the provision of Cysteine to a patient receiving treatment for weight loss to reverse the undesirable effects of non-responsiveness to ongoing drug therapy.

Still another advantage of the present invention is the provision of Cysteine to a patient receiving treatment for weight loss to reverse the undesirable effects which may arise where the patient has a history of exposure to toxins both in and out of the work place.

Still another advantage of the present invention is the provision of Cysteine to a patient receiving treatment for weight loss to reverse the undesirable effects of fat stores becoming saturated with fat-soluble toxins which may leach into a patient's system.

Still another advantage of the present invention is the provision of Cysteine to a patient receiving treatment for weight loss to reverse undesirable effects which may occur due to leaching of fat-soluble toxins such as skin eruptions and depletion of the catecholamine system, where depletion of the catecholamine system may in turn cause tachyphylaxis.

Still another advantage of the present invention is the provision of Cysteine to a patient receiving treatment for weight loss where Cysteine is provided upon initiation of treatment in order to prevent a nutritional deficiency and to maintain the optimal functioning of all of the patients biological systems.

Still another advantage of the present invention is the provision of Cysteine to a patient receiving treatment for weight loss where Cysteine is provided to patients who are not responding to treatment with catecholamine drugs, to effectuate weight loss, or in any other setting where the catecholamine system of the patient is not functioning properly.

Still another advantage of the present invention is the provision of Cysteine to a patient receiving treatment for weight loss where Cysteine is provided to prevent and reverse tachyphylaxis caused from use of catecholamine drugs.

Still another advantage of the present invention is the provision of Cysteine to a patient receiving treatment for weight loss where Cysteine is provided to maintain the proper functioning of the glutathione system for the patient.

Still another advantage of the present invention is the provision of Cysteine to a patient receiving treatment for weight loss where Cysteine is provided to keep the catecholamine system of the patient functioning properly when the patient has a history of exposure to toxins.

Still another advantage of the present invention is the provision of Cysteine to a patient receiving treatment for weight loss where Cysteine is provided to help the catecholamine system to function properly in combination with the serotonin system.

Still another advantage of the present invention is the provision of Cysteine to a patient receiving treatment for weight loss where Cysteine is provided to insure that the body of the patient continues to produce optimal levels of Tyrosine Hydroxylase for proper function of the catecholamine system.

Still another advantage of the present invention is the provision of Cysteine to a patient receiving treatment for weight loss where Cysteine is provided to alleviate undesirable symptoms encountered by patients, once a drug which causes increased levels of norepinephrine in the synapse is terminated.

Still another advantage of the present invention is the provision of Cysteine to a patient receiving treatment for weight loss where Cysteine is provided to restore appetite suppression in patients in weight loss where the patient has experienced problems using the precursors and co-factors of Tyrosine and/or 5-Hydroxytryptophan.

DETAILED DESCRIPTION OF INVENTION

Figure 1:
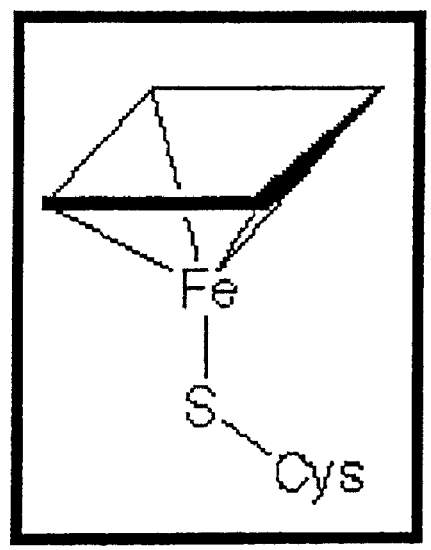
FIG. 1 is a diagram of a Heme-Thiolate Protein.

The comprehensive pharmacological therapy for treatment of obesity involves the combination of medications within "effective dosing ranges" and "optimal dosing ranges". The weight loss therapy in general involves the use of effective dosing ranges of Citalopram and Phentermine; Citalopram and Diethylpropion; Citalopram, Phentermine, and Diethylpropion to effectuate weight loss in a patient.

The use of Citalopram, Phentermine, and Diethylpropion in effective dosing ranges as well as optimum dosing ranges in conjunction with proper replacement of vitamins to counter nutritional deficiency successfully resolves two problems unique to weight loss management programs which use medications. The use of Citalopram, Phentermine, and Diethylpropion in conjunction with nutritional supplements in effective dosing ranges generally achieves acceptable weight loss performance for all patients thereby eliminating the failure of the weight loss program to be effective for five percent to eight percent of the patients who have initiated medication therapy. In addition, the use of Citalopram, Phentermine, and Diethylpropion in conjunction with nutritional supplements in effective dosing ranges also continues to function to assist patients to lose weight beyond a three month period of time thereby solving the problem where 40 percent to 50 percent of the patients undergoing medication therapy encounter a complication where the medication therapy stops working at a plateau which occurs approximately three months on average into the medical treatment.

Through the proper use of effective dosing ranges and nutritional supplementation, generally all patients successfully lose weight from the beginning of therapy and continue to lose weight during medication therapy until a desired goal weight is obtained. In addition, there appears to be no irreversible side effects known during use of the medication combinations of Citalopram, Phentermine and Diethylpropion in conjunction with vitamin supplementation. Proper treatment of weight problems with the disclosed method is highly effective in resolving additional problems caused by or associated with obesity such as diabetes, hypertension, hypercholesterolemia, orthopedic problems, depression, anxiety, panic attacks, migraine headaches and other associated obesity related problems.

The weight loss therapy utilizing medications within an effective therapeutic range and/or optimal dosing range provide superior weight loss results in contrast to weight loss treatment programs implementing a single dose SSRI (Selective Serotonin Reuptake Inhibitor) approach. In the past, the single dose SSRI medication approach to weight loss ceased to provide desired performance for a patient resulting in unacceptable weight loss. The failure of the single dose SSRI therapy to adequately provide a desired level of performance frequently results from the patient having a nutritional deficiency.

The failure of the single dose SSRI therapy to provide for an acceptable level of weight loss frequently occurs because Serotonin and Norepinephrine are two neurotransmitters implicated in weight problems and eating disorders. The chemical pathway for manufacturing Serotonin within a body is:

Tryptophan→Hydroxytryptophan→Serotonin. Vitamin B6 and vitamin C directly and indirectly work as co-factors in this chemical equation.

The chemical pathway for the manufacture of Norepinephrine within the body is Tyrosine→Dopamine→Norepinephrine. Patients who are nutritionally deficient in tryptophan or Tyrosine prior to and/or after initiation of medication therapy may develop Serotonin and/or Norepinephrine deficiencies respectively. Specifically, SSRI medications work with Serotonin and Norepinephrine, such as Phentermine and Diethylpropion, which do not provide adequate performance where a deficiency in Serotonin or Norepinephrine is present. In order to avoid a Serotonin and/or Norepinephrine deficiency a patient under the comprehensive pharmacological therapy for treatment of obesity including Cysteine receives a generic multiple vitamin, 5-Hydroxytryptophan in a range of 50 mg to 900 mg per day, vitamin B6 in a range of 2 mg to 150 mgs per day, vitamin C in a range of 50 mg to 2000 mg per day, and Tyrosine in a range of 50 mg to 4000 mgs per day, as well as calcium in a range of 50 mg to 2000 mgs per day to prevent bone demineralization and Lysine in a range of 50 mg to 2000 mgs per day, which is used to prevent hair loss and other protein metabolism problems while a patient is in a medically induced starvation state of weight management. In addition, a patient may also receive 500 mg to 5000 mg of Cysteine each day and 50 mg to 1000 mg of Selenium each day. The 5 percent to 8 percent of the patients who did not receive any benefit from the initiation of medication therapy under the single dose SSRI treatment regime experience adequate weight loss under the comprehensive pharmacologic therapy for treatment of obesity when a potential nutritional deficiency was treated simultaneously to the introduction of the effective therapeutic range of SSRI medication, Phentermine or Diethylpropion, in conjunction with the vitamin supplementation. In general, all patients experience weight loss under the comprehensive pharmacological therapy when effective therapeutic ranges of SSRI medication, Phentermine and/or Diethylpropion, and/or vitamin supplementation is used.

Within the comprehensive pharmacologic therapy for treatment of obesity the use of Phentermine and/or Diethylpropion in generic form, should be taken concurrently with Citalopram (Celexa), to treat exogenous obesity. Medication combinations that may be used are "Phentermine and Citalopram", "Diethylpropion and Citalopram", and "Phentermine, Diethylpropion and Citalopram". As is known in the art Celxa® is available from Forest Laboratories, Inc., of New York, N.Y., and/or Forest Pharmaceuticals, Inc., of St. Louis, Mo. Citalopram is a racemic mixture of both the enatomers S- and R-Citalopram. The S-Citalopram enatomer is biologically active while the R-enatomer is inactive. As is known in the art, the S-Citalopram enatomer is the SSRI chemical utilized in treating patients. The active S-enantiomer of Citalopram may be separated from the inactive R-enantiomer of Citalopram and individually utilized in treating patients for weight loss. The chemical name for Citalopram is citalopramhydrobromide; (RS)-1-[3-[dimethylamino]propyl]-ρ-fluorophenyl)-5-phthalancarbonitrile, hydrob having the chemical formula $c_{20}h_{22}b_rFN_{20}$.

During the first week the patient is instructed to take 15 mg of generic Phentermine by mouth each morning along with 10 mg of Citalopram for the first 6 days followed by 20 mg of Citalopram thereafter to decrease the gastrointestinal side effects of the Citalopram. Diethylpropion may be used with or without Phentermine in combination with Citalopram in a daily dosing of 75 mg, short or long acting, if increased appetite suppression is desired. A few patients experience tolerability issues with Diethylpropion and a starting dose of 25 mg per day increased incrementally as tolerated to 75 mg per day may be used. The Phentermine should be given in the morning to minimize sleep disturbance, experienced on start-up. The SSRI medications may be given any time during the day with preferential time being at noon. In addition to Citalopram other SSRI medications may include Fluoxetine Hydrochloride (Prosac), Sertralin (Coloft), Fluvoxamine Maleate (Luvox), and Trazodone Hydrochloride (Desyrel).

On start-up, to minimize the possibility of medication ineffectiveness the patient should consume 50 to 200 mg of 5-Hydroxytryptophan a day, Vitamin B6 in the dosing range of 2 to 150 mg per day, Vitamin C in the dosing range of 50 to 2000 mg per day and optionally Tyrosine in the dosing range of 50 to 4000 mg per day as well as Calcium in the dosing range of 50–2000 mg per day and Lysine in the dosing range of 50 to 2000 mg per day.

After the first week of treatment the patients should be evaluated for continued appetite suppression. Appetite suppression may be identified through patient questioning to ascertain "significant hunger", snacking, nibbling, failure to adhere to diet, or using willpower which induces stress to follow the diet. If appetite suppression does not appear to have been obtained, then the medications and/or nutritional supplements may be further adjusted as needed.

At a second visit at the end of the first week of treatment, the patient should have the Phentermine increased from 15 mg taken in the morning to 15 mg taken in the morning and 15 mg taken at noon unless tolerability issues exist, and the Citalopram dosage should now be at a 20 mg daily taken at noon or 10 mg taken at noon and 10 mg taken in the late afternoon (approximately one hour before the last meal of the day).

Citalopram may be increased in 20 mg increments in the "effective therapeutic range" of 20 mg to 80 mg per day. Phentermine is started at 15 mg per day the first week followed by a total daily dosing of 30 mg per day recommended as divided into doses of 15 mg in the morning and 15 mg at noon if no problems with tolerance are noted for the patient. On subsequent visits, Phentermine may be increased to a total daily dosing of 60 mg per day preferably as divided into doses of 30 mg in the morning and 30 mg at noon. The Phentermine has an "effective therapeutic range" of 15 mg to 60 mg per day. The daily "optimal dosing range" for most patients consuming Citalopram is 20 mg to 40 mg per day. The daily "optimal dosage range" for most patients with Phentermine is 30 mg to 60 mg per day.

Citalopram may be provided in a dosing range of 10 mg per day for the first six days of therapy, to minimize start-up side effects, followed by 20 mg per day thereafter. At subsequent visits, if a patient is experiencing low weight loss or significant hunger, Citalopram may be increased in 20 mg increments in the "effective therapeutic range" of 20 mg to 80 mg per day. The Phentermine may have an "effective therapeutic range" of 15 mg to 60 mg per day. Diethylpropion dosage in the amount of 75 mg per day is given. The problems with tolerance develop Diethylpropion dosage may be started at 25 mg per day and increased in 25 mg per week increments to a total daily dosing of 75 mg if "low weight loss" or "significant hunger" is present. The "effective therapeutic range" of Diethylpropion is 25 mg to 75 mg per day. The daily "optimal dosing range" for most patients with Citalopram is 20 mg to 40 mg per day. The "optimal therapeutic range" for most patients for Phentermine is 30 mg to 60 mg per day. The "optimal therapeutic range" for most patients with Diethylpropion is 75 mg per day.

At initiation of therapy the nutritional supplement dosing schedule may be to provide 50 mg to 200 mg of 5-Hydroxytryptophan, 50 mg to 100 mg of vitamin B6, 50 mg to 1000 mg of vitamin C, 500 mg to 1000 mg of Tyrosine, 500 mg to 1000 mg of Lysine, 500 mg to 1000 mg of calcium, 500 mg to 5000 mg of Cysteine and 50 mg to 1000 mg of Selenium. If after the first two visits the patient is experiencing "low weight loss" or "significant hunger" the 5-Hydroxytryptophan may be increased in 100 mg to 300 mg per week increments to a maximum dose of 900 mg per day. If the patient is still refractory to treatment at that point, the Tyrosine may be increased in 500 mg to 1000 mg increments to a maximum dose of 4000 mg per day. Once a patient no longer has "significant hunger" or "low weight loss" the 5-Hydroxytryptophan and Tyrosine may be incrementally decreased back to starting doses or to the lowest dose needed to insure that the patient does not again resume "significant hunger" or "low weight loss".

Patients should further schedule follow up appointments no more than every 2 weeks. At any patient visit should the patient be experiencing "low weight loss" or "significant hunger", the patient should schedule a follow up visit in 1 week.

"Low weight loss" is defined as:
1. Formula 1=[(((weight at previous visit+current weight)/2)×10)−((weight loss since last visit×3,500)/number of days since last visit)]
2. Formula 2=[((goal weight*10)×0.8929)]
3. When the answer to Formula 1 is greater than the answer to Formula 2 the patient has "low weight loss".

After the second visit if the patient still is experiencing "significant hunger", then the Citalopram should be increased to 40 mg. At subsequent visits if "significant hunger" is still present Citalopram may be increased incrementally to 80 mg per day total dosing. The Phentermine may also be increased incrementally to 60 mg per day total dosing (generally given as 30 mg in the morning and 30 mg at noon). The Diethylpropion may be increased incrementally to 75 mg per day total dosing if regular release is utilized.

During subsequent visits while the medications are being increased, the nutritional supplements should also be adjusted. The patient should be consuming the basic doses of Vitamin B6, Vitamin C, as well as Tyrosine, Calcium, a multi-vitamin and Lysine. The 5-Hydroxytryptophan should be increased incrementally in 50 to 300 mg doses from 50, 100, 200, or 300 mg starting doses in 100 mg to 300 mg increments to a maximum dosing of 900 mg per day following each visit as the patient continues to express hunger. Once the patients are in adequate appetite suppression for 7–10 days, the 5-Hydroxytryptophan may be decreased to the first initial dose below which the patient experienced appetite suppression that being 300 or 100 mg per day. The 300 mg dose should be maintained at that level for 2–3 weeks prior to trying to decrease the dosage further to 100 mg per day of 5-Hydroxytryptophan. If at any time the patient does begin to experience hunger after lowering 5-Hydroxytryptophan doses, then the daily dose should be increased back to the dosage that induced full appetite suppression. It should be noted that for patients who have previously consumed 5-Hydroxytryptophan for appetite suppression successfully, and who have terminated the consumption of 5-Hydroxytryptophan and experienced hunger, then the patient will likely be required to restart the consumption of 5-Hydroxytryptophan from the initial dose and duplicate the amount of time necessary to return to full appetite suppression. For example, a patient who initially received 20 days of additional 5-Hydroxytryptophan to obtain appetite suppression and where the patient was no longer taking the additional 5-Hydroxytryptophan following a loss of appetite suppression which resulted in the return of hunger then, the patient will likely be required to receive 20 additional days of 5-Hydroxytryptophan to once again return to full appetite suppression. All patients consuming 5-Hydroxytryptophan should be encouraged to increase the dosage of 5-Hydroxytryptophan if hunger is experienced upon the lowering of the dosage.

Once a patient has obtained adequate appetite suppression through increased dosage of Citalopram within the "effective therapeutic range" of 10 mg to 80 mg per day, and with regulation of nutritional supplements, an attempt should be made within 1 to 3 months after appetite suppression is induced to lower the patient's Norepinephrine and SSRI medication dosage. Many patients at the point in time are able to be maintained on lower dosages of SSRI medication through nutritional supplementation which enhance the underlying Serotonin and Norepinephrine levels.

As the patients are treated with weight management, calorie prescriptions may be needed to ensure that the patient is fully cognizant of their food intake while in appetite suppression. Calorie prescriptions are not only important from the aspect that the patients will lose optimal weight by eating at their calorie prescription, but it is also important to make sure the patients are consuming enough food and not entering into a starvation state with subsequent ketosis which is cardiotoxic. A calorie prescription developed may be:
1. CALRX=((goal weight (which in most cases we use the high end weight on the Metropolitan Tables)×10)−500).

Patients should use ketostix at least once daily to ensure that they are not going into a true starvation state and experiencing ketosis. Exposure to a deep state of ketosis for a long period of time may be fatal from cardiac dysrhythmia.

An initial medical work-up for patients may include a thyroid panel. Approximately 12.5% of patients having obesity problems also have never been properly diagnosed for a hypothyroid abnormality. It may also be beneficial to perform a chem-screen panel to ensure that electrolyte balance and organ function is intact prior to inducing patients into a medical starvation state of weight loss. A cell blood count, a urine analysis, as well as an EKG may also assist to insure that there are no underlying heart problems which may be exacerbated by very low calorie diet.

With regards to exercise, patients are instructed that, "exercise is not to lose weight, it is to tone the body". Patients are already losing optimal weight through the calorie prescription. If patients desire to receive a high intensity work-out the patients will be required to eat more food to ensure that they do not go into ketosis from lowering their effective caloric intake by burning extra calories.

With regards to treatment of type II Diabetes, most diabetics may terminate insulin consumption safely with initiation of therapy. Patients should be switched over to maximum dose double oral hypoglycemic therapy and evaluate their blood sugars four times a day. Further the patients may be placed on a sliding scale with regular insulin where the patient may respond to each individual blood sugar reading with appropriate levels of Regular insulin should their blood sugars be elevated. Most type II diabetics will need no further shots of insulin after initiation of therapy. There is a need for moderately good control of Diabetes prior to initiation of therapy. As type II diabetics continue to lose weight most reach a point where all diabetes medications may be withdrawn. Patients with blood sugars that are relatively high should have them brought under control prior to initiation of therapy.

If weight loss is low during therapy and the patient claims that they are in good appetite suppression and not experiencing "significant hunger", the patient's calorie counting should be vigorously evaluated and proper teaching undertaken with the patient as well as considerations made for increasing the patients medication and/or nutritional supplement dosing as previously discussed.

After a patient reaches goal weight or ideal body weight, the patient needs to be individually assessed for long term maintenance to prevent weight regain. If the patient has a history of having medically dieted in the past and gaining significant weight back, these patients may simply be maintained on lower doses of medications. If the patient does not have a history of medically dieting in the past, then the medications may be removed for four to eight weeks in order to evaluate the continuing need for medications to maintain weight loss. The medications for patients placed directly on maintenance and continued on medications, should be reduced progressively back at 2 week increments to the lowest possible level to maintain weight. While on maintenance a patient should continue on nutritional supplementation as described previously. Any of the previously discussed combinations of medications are acceptable in maintenance as long as the patient tolerates the combination and is effective maintaining weight loss.

As far as standards for implementing care in patients the "Body Mass Index" (BMI) is used. The BMI is defined as the body weight in kilograms divided by the square of the height in meters. If the patients have BMI of 30 or above they are a candidate for weight therapy and if the BMI is 25 or above with significant co-morbidity such as Diabetes, Hypertension, Hypercholesterolemia, they patient can be treated at a BMI of 25 or greater.

There are numerous medical counter indications to weight therapy including severe tremor, uncompensated for Schizophrenia, Active tachycardia, Severe narrowing of Glaucoma, Symptomatic gall stones, obstructive enlarged prostate, history of allergy intolerance to Phentermine or SSRI medication, or Diethylpropion, Diabetes out of control, severe hypertension, angina pectoris, recurrent myocardial infarction, congestive heart failure, epilepsy, hyperthyroidism. In addition patients taking the medications Beta blockers, Theophylline, Ritalin, oral Beta-agonist should not take weight loss medications in addition to these other medications. Caffeine in the diet should also be reduced.

The adjustment of SSRI medications within a dosing range is much more effective than utilization of a single dose of medicine to treat all patients. By increasing medications in the dosing range and using nutritional supplements an effective appetite suppression may be induced with all patients, including patients who are new to therapy and those patients who have prior experience with the medications.

The treatment of a patient for weight loss may include the use of Cysteine with precursors Tyrosine, 5-Hydroxytryptophan, vitamin C, vitamin B6, and calcium. Use of the precursors and co-factors of Cysteine generally insures that adequate direct precursors are available to increase catecholamine levels for a patient prolonging the effectiveness of medication therapy.

The core of Tyrosine Hydroxylase is a "heme-thiolate" protein (see FIG. 1). The "heme-thiolate" protein is composed of iron in the form of a cytochrome P-450 complex and Cysteine. Patients experiencing tachyphylaxis from drugs which cause increased levels of norepinephrine in the synapse, generally have serum iron levels which are normal. Patients who are experiencing tachyphylaxis from drugs which cause increased levels of norepinephrine in the synapse respond to Cysteine therapy, which in turn is effective in reversing the tachyphylaxis.

Cysteine with or without other precursors in the neurotransmitter system may resolve tachyphylaxis and in the process increase catecholamine levels to provide optimal results in patients receiving treatment for obesity. Cysteine with or without other precursors in the neurotransmitter system may include, but are not necessarily limited to Tyrosine and co-factors of Tyrosine which may include but are not necessarily limited to vitamin C, calcium, and vitamin B6.

The intersynaptic levels of norepinephrine may increase by as much as 2,500 times or more with drugs such as Phentermine which are used in the treatment of a patient for weight loss.

Depletion of Cysteine may occur not only from the norepinephrine to Tyrosine Hydroxylase feedback loop, but Cysteine may also be depleted by the Cysteine/glutathione system, which is the main oxidation pathway in the body. The Cysteine/glutathione system in the presences of toxins may contribute to depletion of the catecholamine system. The depletion of the catecholamine system by drugs which cause increased levels of norepinephrine may further cause dysfunction in the Cysteine/glutathione system and it's ability to properly process toxins in the body.

Cysteine may be used to increase catecholamine production not only in patients who have been taking drugs which increase norepinephrine levels in the synapse, but may also be used in treating a patient who has a history of toxin exposure leading to depletion of the catecholamine system, and further in patients who appear depleted of catecholamines without an obvious cause.

Many patients after termination of treatment involving introduction of a drug that increases intersynaptic levels of catecholamines such as Phentermine experience numerous long term problems which may persist for many months or even years. These problems include, but are not necessarily limited to depression, anxiety, panic attacks, trouble concentrating, premenstrual syndrome, insomnia, headaches, etc. The use of Cysteine with precursors and co-factors effectively control and alleviate these problems.

The use of 5-Hydroxytryptophan, is generally not a precursor of the catecholamine system; but is a precursor of the serotonin system. The serotonin system and the catecholamine system are generally both required to be functioning properly and optimally for a patient, in that the dysfunction of one system may significantly affect the other system. Generally, Cysteine may be added to the precursors and co-factors of Tyrosine to alleviate the problems and complications as identified herein.

The precursors of 5-Hydroxytryptophan and Tyrosine in combination with vitamin C, vitamin B6, and calcium may be used in vitamin therapy and/or in combination with drug therapy to effectuate weight loss in a patient. Cysteine may be combined with the SSRI medications or vitamin's as identified above in the amount of 500 mg to 5,000 mg per day. In addition, Selenium in the amount of 50 mcg to 1,000 mcg per day may be added with the Cysteine. Cysteine may have the ability to concentrate mercury into the central nervous system, and Selenium is noted for it's ability of bind mercury into a biologically unavailable form. The introduction of Cysteine preferably initiates at the inception of therapy. However, Cysteine may be introduced at any time during the treatment of a patient for weight loss.

Patients who are receiving medication which increases the levels of norepinephrine should also receive Cysteine upon the initiation of treatment. Medications which cause an increased level of norepinephrine include but are not necessarily limited to: Thentennine; Diethylpropion; Phendimetrazine; Effexor; Merdia; Phenylpropanolamine; Welbutrin; and Remeron.

At the core of the "Tyrosine Hydroxylase enzyme" is a heme-thiolate protein. This protein is made up of an "iron-Cysteine" complex. FIG. 1, is a graphic representation of the heme-thiolate protein at the core of the Tyrosine Hydroxylase enzyme. In the representation the "S" (sulfur group) is from the cysteine group (cyx). The iron group is part to the cytochrome P-450 system.

The above Examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is:

1. A method to facilitate weight loss for a patient not suffering from depression, said method comprising administration of a selective Serotonin reuptake inhibitor (SSRI), Phentermine, 5-Hydroxytryptophan and Tyrosine, wherein said SSRI, said Phentermine, said 5-Hydroxytryptophan, and said Tyrosine are administered in an effective therapeutic range to effectuate weight loss, and wherein said SSRI is selected from the group consisting of Citalopram, S-Citalopram, Fluoxetine Hydrochloride, Sertraline, Fluvozxamine Maleate, and Trazodone Hydrochloride.

2. The method according to claim 1, wherein said Citalopram is Celexa™, said Fluoxetine Hydrochloride is Prozac™, said Sertraline is Zoloft™, said Fluvoxamine Maleate is Luvox™, and said Trazodone Hyrdrochloride is Desyrel™.

3. The method according to claim 1, said effective therapeutic range comprising:
A. the administration of 10 mg of said SSRI each day for a period of six days followed by the administration of a daily dosage of between 10 mg and 80 mg of said SSRI;
B. the administration of 15 mg of said Phentermine each day for said period of six days followed by the administration of a daily dosage of between 15 mg and 60 mg of said Phentemine; and
C. the administration of 50 mg to 900 mg of said 5-Hydroxytryptophan each day, and 50 mg to 4000 mg of Tyrosine each day until a target weight for said patient is obtained.

4. The method according to claim 3, wherein said administration of said SSRI and the administration of said Phentermine is increased when said patient experiences low weight loss, said low weight loss comprising:
A. said patient weight at a previous visit plus said patient current weight first divided by 2 and then multiplied by 10, less said current patient weight, less said patient weight at said previous visit, multiplied by 3500, divided by the number of days between the date of the previous visit and the date of said current weight for the provision of a first sum;

B. calculating a second sum by multiplying a patient goal weight by 10 and then divided 0.8929; and C. comparing said first sum to said second sum where low weight loss occurs when said first sum is larger than said second sum.

5. The method according to claim 3, further comprising the administration of 50 mcg to 1000 mcg of Selenium each day.

6. The method according to claim 3, further comprising the administration of:

A. Vitamin B6;
B. Vitamin C;
C. Calcium; and
D. Lysine.

7. The method according to claim 6, further comprising the administration of:

A. 2 mg to 150 mg of Vitamin B6 each day;
B. 50 mg to 2000 mg of Vitamin C each day;
C. 50 mg to 2000 mg of Calcium each day; and
D. 50 mg to 2000 mg of Lysine each day.

8. The method according to claim 1 further comprising the administration of Cysteine wherein said Cysteine is administered in an effective therapeutic range to effectuate weight loss.

9. The method according to claim 8, said effective therapeutic range comprising the administration of 500 mg to 5000 mg of Cysteine each day until a target weight for said patient is obtained.

10. A method to facilitate weight loss for a patient not suffering from depression, said method comprising administration of a selective Serotonin reuptake inhibitor (SSRI), Phentermine, 5-Hydroxytryptophan and Tyrosine, wherein said SSRI, said Phentermine, said 5-Hydroxytryptophan, and said Tyrosine are administered in an effective therapeutic range to effectuate weight loss wherein the concentration level of neurotransmitters for the patient is elevated with respect to a previous concentration level of neurotransmitters for said patient, and wherein said SSRI is selected from the group consisting of Citalopram, S-Citalopram, Fluoxetine Hydrochloride, Sertraline, Fluvoxamine Maleate, and Trazodone Hydrochloride.

11. A method according to claim 10, wherein said Citalopram is Celexa™, said Fluoxetine Hydrochloride is Prozac™, said Sertraline is Zoloft™, said Fluvoxamine Maleate is Luvox™, and said Trazodone Hyrdrochloride is Desyrel™.

12. The method according to claim 10, said effective therapeutic range comprising:

A. the administration of 10 mg of said SSRI each day for a period of 6 days followed by the administration of a daily dosage of between 10 mg and 300 mg of said SSRI;

B. the administration of 15 mg of said Phentermine each day for said period of 6 days followed by the administration of a daily dosage of between 15 mg and 60 mg of said Phentermine; and C. the administration of 50 mg to 900 mg of said 5-Hydroxytryptophan each day, and 50 mg to 4000 mg of Tyrosine each day until a target weight for said patient is obtained.

13. The method of claim 12, further comprising the administration of Vitamin B6, Vitamin C, a multi-vitamin, Calcium, and Lysine.

14. The method according to claim 13, further comprising the administration of:

A. 2 mg to 150 mg of Vitamin B6 each day;
B. 50 mg to 2000 mg of Calcium each day;
C. 50 mg to 2000 mg of Lysine each day; and
D. 50 mg to 2000 mg of Vitamin C each day.

15. The method according to claim 14, wherein said administration of said SSRI and the administration of said Phentermine is increased when said patient experiences low weight loss, said low weight loss comprising:

A. said patient weight at a previous visit plus said patient current weight first divided by 2 and then multiplied by 10, less said current patient weight, less said patient weight at said previous visit, multiplied by 3500, divided by the number of days between the date of the previous visit and the date of said current weight for the provision of a first sum;

B. calculating a second sum by multiplying a patient goal weight by 10 and then divided 0.8929; and C. comparing said first sum to said second sum where low weight loss occurs when said first sum is larger than said second sum.

16. The method according to claim 14, further comprising the administration of 50 mg to 1000 mg of Selenium each day.

17. The method according to claim 10, further comprising the administration of Cysteine wherein said Cysteine is administered in an effective therapeutic range to effectuate weight loss.

18. The method according to claim 17, said effective therapeutic range comprising the administration of 500 mg to 5000 mg of Cysteine each day until a target weight for said patient is obtained.

* * * * *